US00RE38683E

(19) United States
(12) Reissued Patent
Sullivan

(10) Patent Number: US RE38,683 E
(45) Date of Reissued Patent: Jan. 4, 2005

(54) PREPARATION OF TITANOCENES

(75) Inventor: Jeffrey M. Sullivan, Loveland, CO (US)

(73) Assignee: Boulder Scientific Company, Mead, CO (US)

(21) Appl. No.: 10/053,997

(22) Filed: Jan. 19, 2002

Related U.S. Patent Documents

Reissue of:
(64) Patent No.: 5,847,176
Issued: Dec. 8, 1998
Appl. No.: 08/885,805
Filed: Jun. 30, 1997

U.S. Applications:
(63) Continuation-in-part of application No. PCT/US96/18666, filed on Nov. 22, 1996.

(51) Int. Cl.[7] ..... C07F 17/00; C07F 7/28

(52) U.S. Cl. ..... 556/11; 556/53; 526/160; 526/943; 502/103; 502/117

(58) Field of Search ..... 556/11, 53; 502/103, 502/117; 526/160, 943

(56) References Cited

U.S. PATENT DOCUMENTS 5,329,033 A * 7/1994 Spaleck et al. ..... 556/53
5,693,836 A * 12/1997 Winter et al. ..... 556/11

OTHER PUBLICATIONS

Ewen et al., Macromol. Rapid Commun., vol. 19, No. 1, pp. 71–73, 1998.*

* cited by examiner

*Primary Examiner*—Porfirio Nazario-Gonzalez
(74) *Attorney, Agent, or Firm*—Edwards S. Irons

(57) ABSTRACT

A method for producing dialkylsilyl*bis*(2-alkyl-4-aryl indenyl) titanocenes including rac-$Me_2Si$*bis*(2-methyl-4-phenylindenyl)-titanium dichloride is described.

5 Claims, 1 Drawing Sheet

PREPARATION OF TITANOCENES

Matter enclosed in heavy brackets [ ] appears in the original patent but forms no part of this reissue specification; matter printed in italics indicates the additions made by reissue.

RELATED APPLICATION

This application is a continuation-in-part of Blankenship application PCT/US96/18666 filed 22 Nov., 1996 and incorporated herein by reference.

FIELD OF INVENTION

This invention relates to the preparation of [chiral] titanocenes. More particularly, the invention relates to dialkylsilyl*bis*(2-alkyl-4-arylindenyl) metallocenes.

BACKGROUND OF THE INVENTION

U.S. Pat. No. 5,629,254 at column 29, line 5, et. seq., describes compounds of the Formula Ia:

Ia

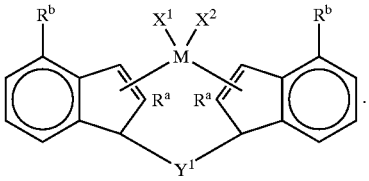

in which $R^a$ may be a 1 to 20 carbon atom hydrocarbon group, ($R^b$) may be a 6 to 16 carbon atom aryl group, M may be titanium, zirconium or hafnium. $X^1$ and $X^2$ may be a halogen atom and $Y^1$ may be a divalent-silicon containing group.

There may also be used the transition metal compounds obtained by substituting titanium metal of hafnium metal . . . for zirconium metal in the above-exemplified compounds. [Col. 32, 11. 5–9]

It appears that the sole reference to a method which may be useful for preparing the Formula Ia compounds is found at column 13, lines 21–25 of U.S. Pat. No. 5,629,254 which states:

The transition metal compounds according to the present invention can be prepared in accordance with the methods described in Journal of Organometallic Chem. 288 (1985), pages 63 to 67, European Patent Publication No. 0,320,762 specification and Examples thereof . . . .

Neither reference specifically exemplifies the synthesis of any titanocene. Nor does any working example of U.S. Pat. No. 5,629,254 do so.

SUMMARY OF THE INVENTION

This invention provides a method for preparing the titanocene compounds of Formula Ia.

In a first step, a 2-alkyl-4-aryl indene is converted to a dialkali metal salt, preferably a dilithium salt.

The dialkali metal salt is then reacted in a second step with a dihalodialkyl silane to produce a bis-indenyl compound of Formula II:

II

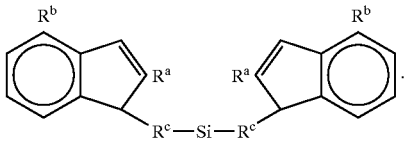

in which $R^a$ and $R^b$ are as described with respect to Formula Ia and in which $R^c$ is a one to ten carbon atom alkyl group.

In a third step, the Formula II compound is combined with a titanium trichloride ($TiCl_3$) containing mixture formed by reacting titanium tetrachloride ($TiCl_4$) with an alkali metal alkyl compound, wherein a metallocene ligand is produced in which titanium is present in a plus three oxidation state. The titanium is oxidized to the plus four state, for example, by reaction with cuprous chloride or chloroform, wherein a reaction mixture which [contains] *contain* the desired titanocene of Formula III is produced.

III

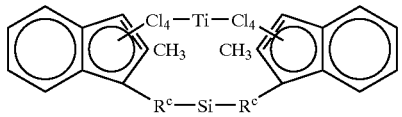

DETAILED DESCRIPTION OF THE INVENTION

Figure 1:
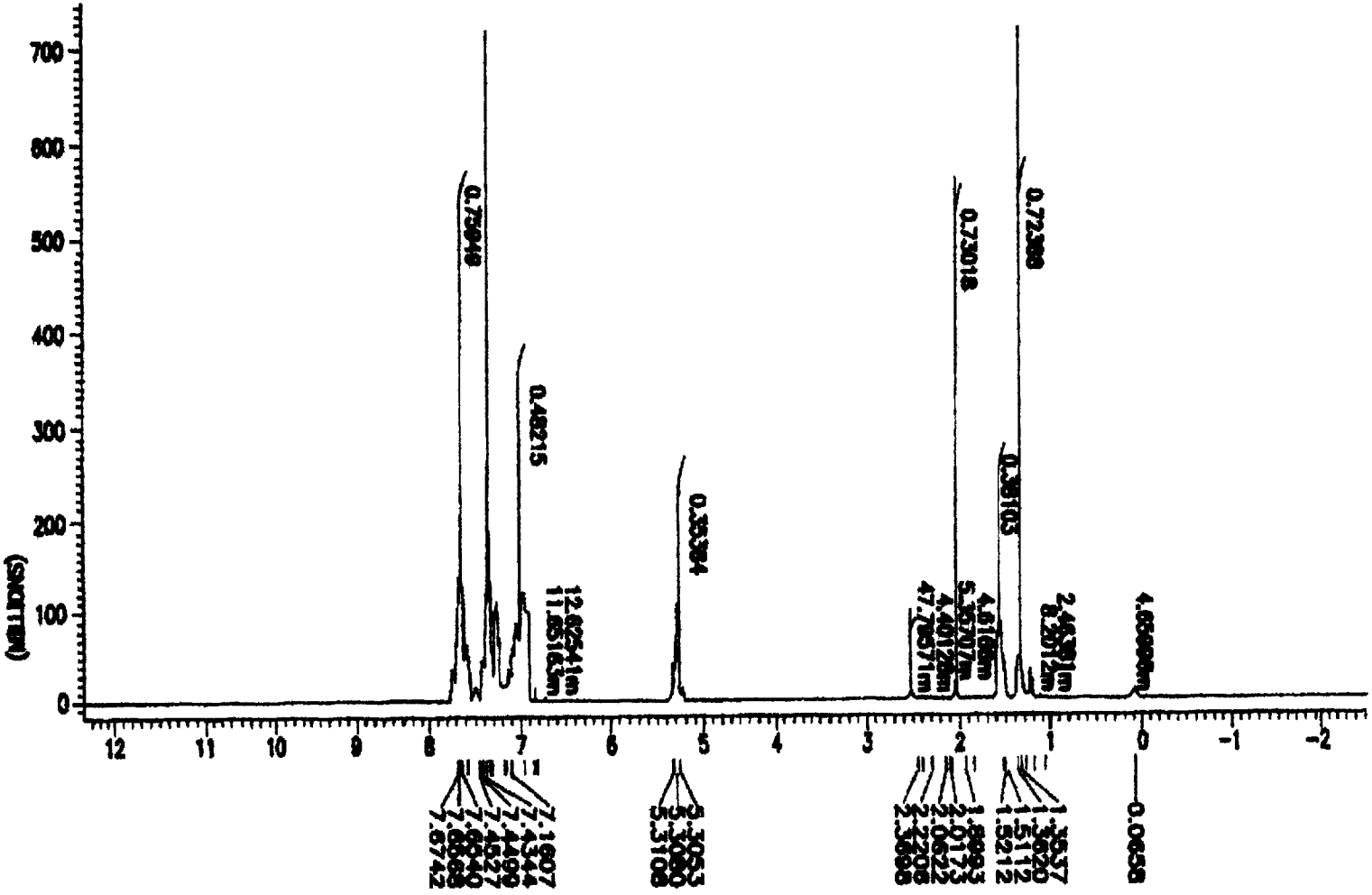
FIG. 1 is a proton nuclear magnetic resonance (NMR) spectrum of rac-dimethylsilyl(2-methyl-4-phenyl indenyl) titanium dichloride acquired with a JEOL Eclipse 400 NMR spectrometer prepared by the method of the sample labelled 552-001(c).3.

A typical Formula Ia titanocene synthesis includes a first step in which a 2-alkyl-4-aryl indene having the Formula IV:

IV

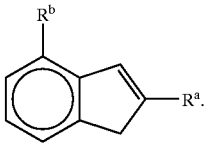

in which $R^a$ and $R^b$ are as previously described and which is reacted in a first reaction vessel with an alkali metal alkyl compound having the formula RM in which R is a straight or branched chain 2 to 10 carbon atom alkyl group and M is sodium, potassium or, preferably, lithium to provide a first reaction mixture which contains a dialkali metal salt of the Formula II compound. The reactants are combined in substantially stoichiometric amounts in a non-interfering, preferably hydrocarbon, medium.

Useful hydrocarbon media include aliphatic or aromatic hydrocarbons such as hexane, heptane, cyclohexane, benzene, toluene and xylene. Toluene is preferred.

In a second step, titanium tetrachloride in a second reaction vessel is reacted as in the first step in a non-interfering, preferably hydrocarbon medium as in the first step with an alkali metal alkyl compound RM to produce a second reaction mixture containing titanium trichloride.

The titanium trichloride containing mixtures are produced by the preferably stoichiometric (1:1) reaction of an organometallic compounds, such as n-butyl lithium or n-butyl magnesium chloride, with titanium tetrachloride in the non-interfering solvent medium. These mixtures are used directly without isolation of the titanium trichloride.

In a third step the first and second reaction mixtures are combined, for example, in the second reaction vessel for reaction to produce a titanocene catalyst ligand in which titanium is present in a plus three oxidation state. An oxidizing agent, e.g., cuprous chloride or chloroform, is added with agitation to produce a third reaction mixture in which the desired titanocene of Formula III is present as a mixture of rac solid and meso isomers.

The isomer mixture is separated from the reaction mixture and dried. The dry mixture of rac and meso isomers is resolved, for example, by treatment with a selective solvent preferably for the meso isomer to provide the rac isomer in substantially pure form. The isomer mixture may also be resolved by the method described in Gately application entitled "Preparation and Separation of Rac and Meso Compound Mixtures" filed Jun. 9, 1997.

EXAMPLE 1

Preparation of Rac $Me_2Si$*Bis*(2-Methyl-4-Phenylindenyl)-Titanium Dichloride A first flask was charged with toluene (300 mL) and tetrahydrofuran (THF) (15 g, 0.2 mol) and 2-methyl-4phenylindene (21.2 g, 0.2 mol). The mixture was cooled to −20° C. followed by the addition of 1.6M butyllithium in hexanes (125 mL). The mixture which contained 2-methyl-4-phenylindene lithium was warmed to 25° C. and stirred for four hours. The stirred contents were cooled to −20° C. and dichlorodimethylsilane (12.9 g) was added. The reaction mixture so formed was warmed to 25° C. and stirred for 12–16 hours and then cooled to −20° C. 1.6M butyllithium in hexanes (125 mL) was added and the contents of the first flask were then warmed to 25° C. and stirred for eight hours. The first flask reaction mixture contained the dilithium salt of $Me_2Si$ bis(2-methyl-4-phenylindene).

A second flask was charged with heptane (300 mL) and titanium tetrachloride (18.9 g, 0.1 mol). 1.6M butyllithium in hexanes (62.5 mL, 0.1 mol) was slowly added maintaining the temperature below 25° C., for example, 0° C. to 20° C. THF (100 g) were added. The reaction mixture was stirred for two hours. The contents were cannulated to the dilithium salt in the first flask and the mixture stirred for two hours at 25° C. CuCl (2 g, cuprous chloride) was added and the mixture was stirred for two hours at 25° C. The solids were separated from the reaction mixture by filtration, washed with hexanes (50 mL) and then dried in a vacuum.

The dry solids were dissolved with dichloromethane (500 mL) and the solutions filtered through a small bed of celite. The volume of the filtrate was reduced to 50–75 mL. The crystals separated by filtration were washed with 20 mL of dichloromethane, and dried in vacuum. Yield=9–15 g. 15/20% yield of rac $Me_2Si$*bis*(2-methyl-4-phenylindenyl)-titanium dichloride having the same NMR spectrum as FIG. 1.

EXAMPLE 2

Preparation of Rac $Me_2Si$*Bis*(2-Methyl-4-α-Naphthylindenyl)-Titanium Dichloride Example 1 is repeated with the 2-methyl-4-α-naphthylindenyl used as a first flask reactant instead of 2-methyl-4-phenylindene.

EXAMPLE 3

Preparation of Rac $Me_2Si$*Bis*(2-Methyl-4-Anthracenyl Indene)-Titanium Dichloride Example 1 is repeated with the 2-methyl-4-anthracenyl indene used as a first flask reactant instead of 2-methyl-4-phenylindene.

I claim:

1. A method for preparing a dialkylsilyl*bis*(2-alkyl-4-arylindenyl) titanium dichloride which comprises:

(i) reacting a 2-alkyl-4-arylindene with an alkali metal alkyl and a dihalodialkyl silane to provide a first reaction mixture in a first reaction vessel;

(ii) separately reacting in a second reaction vessel titanium tetrachloride [with] *and* a second alkali metal alkyl which may be the same as or different from said first alkali metal alkyl to provide a second reaction mixture [containing titanium trichloride in said second reaction vessel];

wherein said [second] *first* reaction mixture contains a ligand of said dialkylsilyl*bis*(2-alkyl-4-arylindenyl) titanium dichloride in which titanium is present in a plus three oxidation state;

(iii) containing said first and second reaction mixtures in the presence of an oxidizing agent;

wherein a third reaction mixture containing a mixture of rac and meso forms of said dialkylsilyl*bis*(2-alkyl-4-arylindenyl) titanium dichloride is produced.

2. The claim 1 method further comprising (iv) separating said mixture of rac and meso forms of said dialkylsilyl (2-alkyl-4-arylindenyl) titanium dichloride from said third reaction mixture.

3. The claim 2 process further comprising separating said mixture of rac and meso forms of said dialkylsilyl (2-alkyl-4-arylindenyl) titanium dichloride from said third reaction mixture; and (v) separating said rac from said meso form of said dialkylsilyl (2-alkyl-4-arylindenyl) titanium dichloride.

4. The claim 1 method in which said 2-alkyl-4-arylindene reacted in step (i) is 2-methyl-4-phenyl indene or 2-methyl-4-naphthyl indene or 2-methyl-4-anthracenyl indene and said step (iii) third reaction mixture contains a mixture of rac and meso forms of 2-methyl-4-phenyl indene or 2-methyl-4-naphthyl indene or 2-methyl-4-anthracenyl indene.

5. The claim 1 method wherein said 2-alkyl-4-arylindene reacted in step (i) is 2-methyl-4-phenyl indene wherein said first and second alkali metal alkyls are each n-butyl lithium and wherein said step (iii) oxidizing agent is cuprous chloride or chloroform.

[6. Rac-$Me_2Si$(2-methyl-4-phenylindenyl)-titanium dichloride.]

* * * * *